(12) United States Patent
Hata et al.

(10) Patent No.: US 12,337,187 B2
(45) Date of Patent: Jun. 24, 2025

(54) IRRADIATION DEVICE AND TREATMENT METHOD

(71) Applicant: TERUMO KABUSHIKI KAISHA, Tokyo (JP)

(72) Inventors: Mayu Hata, Kanagawa (JP); Keiko Otsu, Kanagawa (JP); Satoru Suehara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 560 days.

(21) Appl. No.: 17/704,428

(22) Filed: Mar. 25, 2022

(65) Prior Publication Data

US 2022/0219009 A1 Jul. 14, 2022

Related U.S. Application Data

(63) Continuation of application No. PCT/JP2020/037150, filed on Sep. 30, 2020.

(30) Foreign Application Priority Data

Sep. 30, 2019 (JP) .................................. 2019-180489

(51) Int. Cl.
*A61N 5/06* (2006.01)

(52) U.S. Cl.
CPC .... *A61N 5/0603* (2013.01); *A61N 2005/0611* (2013.01); *A61N 2005/063* (2013.01);
(Continued)

(58) Field of Classification Search
CPC ...... A61N 5/06–2005/073; A61B 18/20–18/28
See application file for complete search history.

(56) References Cited

U.S. PATENT DOCUMENTS 6,096,030 A 8/2000 Ortiz
6,364,874 B1 * 4/2002 Bays .................... A61N 5/0603
606/15

(Continued)

FOREIGN PATENT DOCUMENTS

JP 2001517507 A 10/2001
JP 2011147580 A 8/2011

(Continued)

OTHER PUBLICATIONS

International Search Report (PCT/ISA/210) with translation and Written Opinion (PCT/ISA/237) mailed on Dec. 1, 2020, by the Japanese Patent Office as the International Searching Authority for International Application No. PCT/JP2020/037150. (15 pages).

(Continued)

*Primary Examiner* — Jonathan T Kuo
(74) *Attorney, Agent, or Firm* — Buchanan Ingersoll & Rooney PC

(57) ABSTRACT

An irradiation device and a treatment method capable of effectively irradiating an antibody-photosensitive substance bound to a cell membrane of cervical cancer with near-infrared light. The treatment method for cervical cancer includes: intravenously administering an antibody-light-absorbing substance; inserting a second irradiation device including a second optical fiber from a vagina into a cervix 12 hours to 36 hours after the intravenous administration; performing irradiation by using the second optical fiber included in the second irradiation device in a direction substantially perpendicular to the second optical fiber; drawing at least a part of a deformation portion included in the second irradiation device to an external uterine ostium and inflating the deformation portion so as to follow a shape of an organ; emitting near-infrared light by using the second optical fiber in a substantially distal direction and/or the (Continued)

direction substantially perpendicular to the second optical fiber; and contracting the deformation portion.

8 Claims, 5 Drawing Sheets

(52) U.S. Cl.
CPC .............. *A61N 2005/0643* (2013.01); *A61N 2005/0659* (2013.01)

(56) References Cited

U.S. PATENT DOCUMENTS

| | | | | |
|---|---|---|---|---|
| 7,498,029 | B2* | 3/2009 | Hasan | ............... C07K 16/2863 |
| | | | | 424/143.1 |
| 2002/0197262 | A1* | 12/2002 | Hasan | ............... A61K 41/0057 |
| | | | | 604/20 |
| 2006/0282132 | A1* | 12/2006 | Arai | ...................... A61N 5/062 |
| | | | | 607/88 |
| 2008/0065003 | A1 | 3/2008 | Neuberger et al. | |
| 2012/0010558 | A1 | 1/2012 | Kobayashi et al. | |
| 2014/0107404 | A1 | 4/2014 | Gruber | |
| 2017/0050043 | A1* | 2/2017 | Kang | ................... A61B 5/0066 |
| 2018/0113246 | A1 | 4/2018 | Rose et al. | |

FOREIGN PATENT DOCUMENTS

| | | |
|---|---|---|
| JP | 2014523907 A | 9/2014 |
| JP | 2016214373 A | 12/2016 |
| WO | 2018/080952 A1 | 5/2018 |
| WO | 2020138138 A1 | 7/2020 |

OTHER PUBLICATIONS

English Translations of the International Search Report (Form PCT/ISA/210) issued Dec. 1, 2020, by the Japanese Patent Office in corresponding International Application No. PCT/JP2020/037150. (3 pages).

English Translations of the International Preliminary Report on Patentability (Form PCT/IPEA/409) issued Oct. 6, 2021, by the Japanese Patent Office in corresponding International Application No. PCT/JP2020/037150. (4 pages).

* cited by examiner

IRRADIATION DEVICE AND TREATMENT METHOD

CROSS-REFERENCES TO RELATED APPLICATIONS

This application is a continuation of International Application No. PCT/JP2020/037150 filed on Sep. 30, 2020, which claims priority to Japanese Application No. 2019-180489 filed on Sep. 30, 2019, the entire content of both of which is incorporated herein by reference.

FIELD OF THE DISCLOSURE

The present disclosure relates to an irradiation device used for treatment of cervical cancer and a treatment method for cervical cancer.

BACKGROUND DISCUSSION

The number of patients with cervical cancer has an increasing tendency, and in particular, the number of young female patients in their 20s and 30s is increasing. In current treatment of cervical cancer, a standard treatment is to remove an entire uterus from an early stage (stage I), however, for younger patients, a local treatment is desired to preserve the uterus in order to maintain fertility. Further, in an advanced stage (stage III and subsequent stages), when cancer has spread to surrounding tissues and is difficult to remove by surgery, and thus a standard treatment is to combine radiation therapy and chemotherapy. However, a five-year survival rate can be as low as 50% in stage III and 20% in stage IV, and more effective treatment is desired. As the local treatment for cancer, a treatment method using a photoreactive substance is known. In particular, a treatment method using an antibody-photosensitive substance (hydrophilic phthalocyanine) can specifically kill target cells without killing non-target cells such as normal cells by irradiating the antibody-photosensitive substance accumulated in tumor with near-infrared light, and can be expected to achieve a high treatment effect while reducing side effects.

Meanwhile, in order to achieve a high treatment effect by the antibody-photosensitive substance, the antibody-photosensitive substance adsorbed to the tumor is required to be reliably irradiated with near-infrared light. However, near-infrared light has a small penetration depth, and thus can be difficult to deliver from a body surface to a solid cancer in a relatively noninvasive manner. Accordingly, it would be desirable to have a method for reliably irradiating a tumor in a body with light with reduced invasiveness. In the case of cervical cancer, cancer often spreads over a wide area of a cervical canal, and a method for irradiating cancer in a relatively wide range with light from as close as possible is required. Further, depending on the advanced stage, cancer may reach a pelvic wall, in which case it is difficult for light to approach the pelvic wall by a minimally invasive method that is transvaginal or uses a laparoscope. For example, United States Patent Application Publication No. 2018/0113246 discloses a method of transvascularly inserting an elongated device including an optical fiber to a position near a tumor so as to emit light from the inside of a blood vessel.

SUMMARY

An irradiation device and a treatment method capable of effectively irradiating an antibody-photosensitive substance bound to cell membranes of cervical cancer with near-infrared light are disclosed.

In accordance with one aspect, a treatment method is disclosed for cervical cancer, including: intravenously administering an antibody-light-absorbing substance; inserting a first irradiation device, including a first optical fiber and an orientation marker, into a uterine artery 12 hours to 36 hours after the intravenous administration; advancing the first irradiation device to a target position while confirming a position of the first irradiation device with the orientation marker; emitting near-infrared light by using the first optical fiber in a direction substantially perpendicular to the first optical fiber; removing the first irradiation device out of a body; inserting a second irradiation device, which is the first irradiation device or another irradiation device, from a vagina into a cervix; performing irradiation by using a second optical fiber included in the second irradiation device in a direction substantially perpendicular to the second optical fiber; drawing at least a part of a deformation portion included in the second irradiation device to an external uterine ostium and inflating the deformation portion so as to follow a shape of an organ; emitting near-infrared light by using the second optical fiber in a substantially distal direction and/or the direction substantially perpendicular to the second optical fiber; and contracting the deformation portion.

In the treatment method configured as described above, the first irradiation device is inserted into the uterine artery to emit near-infrared light from the inside of a blood vessel in the substantially vertical direction, so that a tissue or an organ infiltrated with cancer cells near the uterine artery can be effectively irradiated with near-infrared light. Further, in this treatment method, the second irradiation device is inserted into the cervix to emit near-infrared light in the substantially vertical direction, so that cancer cells in the cervix can be effectively irradiated with near-infrared light from a lumen of the cervix. Furthermore, in this treatment method, the deformation portion drawn from the external uterine ostium is inflated to emit near-infrared light in the distal direction and/or the vertical direction, so that cancer cells near the uterine vagina can be effectively irradiated with near-infrared light. Therefore, in this treatment method, the antibody-photosensitive substance bound to cell membranes of cervical cancer can be effectively irradiated with near-infrared light.

In accordance with another aspect, a treatment method is disclosed for cervical cancer, including: intravenously administering an antibody-light-absorbing substance; inserting a first irradiation device, including a first optical fiber and an orientation marker, into a uterine artery 12 hours to 36 hours after the intravenous administration; advancing the first irradiation device to a target position while confirming a position of the first irradiation device with the orientation marker; emitting near-infrared light by using the first optical fiber in a direction substantially perpendicular to the first optical fiber; removing the first irradiation device out of a body; inserting a second irradiation device, which is the first irradiation device or another irradiation device, from a vagina into a cervix; inflating a deformation portion included in the second irradiation device so as to follow a shape of an organ; emitting near-infrared light by using a second optical fiber in a substantially distal direction and/or a direction substantially perpendicular to the second optical fiber; and contracting the deformation portion.

In the treatment method configured as described above, the first irradiation device is inserted into the uterine artery to emit near-infrared light from the inside of a blood vessel in the substantially vertical direction, so that a tissue or an organ infiltrated with cancer cells near the uterine artery can be effectively irradiated with near-infrared light. Further, in this treatment method, the second irradiation device is inserted into the cervix and the deformation portion is inflated to emit near-infrared light in the distal direction and/or the vertical direction, so that a wide range of cervical cancer in the cervix can be effectively irradiated with near-infrared light. Therefore, in this treatment method, the antibody-photosensitive substance bound to cell membranes of cervical cancer can be effectively irradiated with near-infrared light.

In another aspect, a treatment method is disclosed for cervical cancer, including: intravenously administering an antibody-light-absorbing substance; inserting a second irradiation device including a second optical fiber from a vagina into a cervix 12 hours to 36 hours after the intravenous administration; performing irradiation by using the second optical fiber included in the second irradiation device in a direction substantially perpendicular to the second optical fiber; drawing at least a part of a deformation portion included in the second irradiation device to an external uterine ostium and inflating the deformation portion so as to follow a shape of an organ; emitting near-infrared light by using the second optical fiber in a substantially distal direction and/or the direction substantially perpendicular to the second optical fiber; and contracting the deformation portion.

In the treatment method configured as described above, the second irradiation device is inserted into the cervix to emit near-infrared light in the substantially vertical direction, so that cancer cells in the cervix can be effectively irradiated with near-infrared light from a lumen of the cervix. Furthermore, in this treatment method, the deformation portion drawn from the external uterine ostium is inflated to emit near-infrared light in the distal direction and/or the vertical direction, so that cancer cells near the uterine vagina can be effectively irradiated with near-infrared light. Therefore, in this treatment method, the antibody-photosensitive substance bound to cell membranes of the cancer cells of the cervix and a tissue or an organ infiltrated from the cervix in a vertical direction can be effectively irradiated with near-infrared light.

In another aspect of the treatment method according to the disclosure that may be a treatment method for cervical cancer, including: intravenously administering an antibody-light-absorbing substance; inserting a second irradiation device including a second optical fiber from a vagina into a cervix 12 hours to 36 hours after the intravenous administration; inflating a deformation portion included in the second irradiation device so as to follow a shape of an organ; emitting near-infrared light by using the second optical fiber in a substantially distal direction and/or a direction substantially perpendicular to the second optical fiber; and contracting the deformation portion.

In the treatment method configured as described above, the second irradiation device is inserted into a cervical canal and the deformation portion is inflated to emit near-infrared light in the distal direction and/or the vertical direction, so that a wide range of cancer cells in the cervix can be effectively irradiated with near-infrared light. Therefore, in this treatment method, the antibody-photosensitive substance bound to cell membranes of the cancer cells in the cervix and a tissue or an organ infiltrated from the cervix in a vertical direction can be effectively irradiated with near-infrared light.

In this treatment method, in the inflating the deformation portion, a part of the deformation portion may be inflated so as to follow a shape of the uterine vagina on a side proximal of the external uterine ostium. Accordingly, in this treatment method, the antibody-photosensitive substance bound to cell membranes of the cancer cells in the cervix including the uterine vagina and the tissue or the organ infiltrated downward of the cervix can be effectively irradiated with near-infrared light.

In this treatment method, in the inflating the deformation portion, a proximal portion of the deformation portion may be inflated so as to follow the shape of the uterine vagina on the side proximal of the external uterine ostium, and a distal portion of the deformation portion may be inflated so as to follow a shape of a uterine cavity on a side distal of an internal cervical ostium. Accordingly, in this treatment method, the antibody-photosensitive substance bound to the cell membranes of the cancer cells in the cervix and the tissue or the organ infiltrated from the cervix in the vertical direction can be effectively irradiated with near-infrared light.

In this treatment method, rotating the second irradiation device, the inflating the deformation portion so as to follow the shape of the organ, the emitting near-infrared light by using the second optical fiber in the distal direction and/or the direction substantially perpendicular to the second optical fiber, and the contracting the deformation portion may be repeated at least once after the contracting the deformation portion. Accordingly, in this treatment method, a wide area of the cervix in a circumferential direction can be irradiated with near-infrared light.

The second irradiation device may be identical to the first irradiation device. Accordingly, in this treatment method, the irradiation with near-infrared light from the uterine artery and the irradiation with near-infrared light from the cervix can be performed by one irradiation device. Therefore, this treatment method can help improve medical economics.

In this treatment method, after the removing the first irradiation device out of the body, the first irradiation device may be washed. Accordingly, in this treatment method, blood attached to the first irradiation device inserted into the blood vessel is removed, and the first irradiation device can be placed in a desirable state to be inserted from the vagina into the cervix.

In this treatment method, the inflating the deformation portion included in the first irradiation device may be performed before the emitting near-infrared light by using the first optical fiber, and the contracting the deformation portion included in the first irradiation device may be performed after the emitting near-infrared light by using the first optical fiber. Accordingly, when emitting near-infrared light from the first irradiation device in the uterine artery, blood flow in the uterine artery can be blocked. Therefore, an influence of the blood on near-infrared light can be reduced, and a target site can be effectively irradiated with near-infrared light.

In accordance with an aspect, the irradiation device according to the disclosure is an irradiation device configured to be used for treatment of cervical cancer, and, configured to be used for photoimmunotherapy of killing a cancer cell by irradiating an antibody-photosensitive substance bound to a cell membrane of the cancer cell with near-infrared light. The irradiation device can include: an elongated shaft portion; a balloon provided at a distal portion of the shaft portion and configured to inflate; an optical fiber; and an irradiation unit provided at a distal end of the optical fiber, arranged inside the balloon, and configured to emit light. The irradiation unit is configured to emit light in a direction substantially perpendicular to an axis of the optical fiber and in a substantially distal direction.

The irradiation unit may be configured to emit light in a state where the balloon is contracted and in a state where the balloon is inflated.

The balloon may be provided inside with an X-ray opaque orientation marker.

BRIEF DESCRIPTION OF THE DRAWINGS

FIGS. 5A and 5B are schematic views illustrating the irradiation device inserted into a cervix from a vagina, in which FIG. 5A illustrates a state where near-infrared light is emitted from the cervix, and FIG. 5B illustrates a state where a deformation portion drawn from an external uterine ostium is deformed to emit near-infrared light.

FIGS. 7A and 7B are plan views illustrating a first modification of the irradiation device, in which FIG. 7A illustrates a state before a deformation portion is deformed, and FIG. 7B illustrates a state where the deformation portion is deformed.

FIGS. 8A and 8B are plan views illustrating a second modification of the irradiation device, in which FIG. 8A illustrates a state before the deformation portion is deformed, and FIG. 8B illustrates a state where the deformation portion is deformed.

FIGS. 9A and 9B are plan views illustrating a third modification of the irradiation device, in which FIG. 9A illustrates a state before the deformation portion is deformed, and FIG. 9B illustrates a state where the deformation portion is deformed.

DETAILED DESCRIPTION

Figure 1:
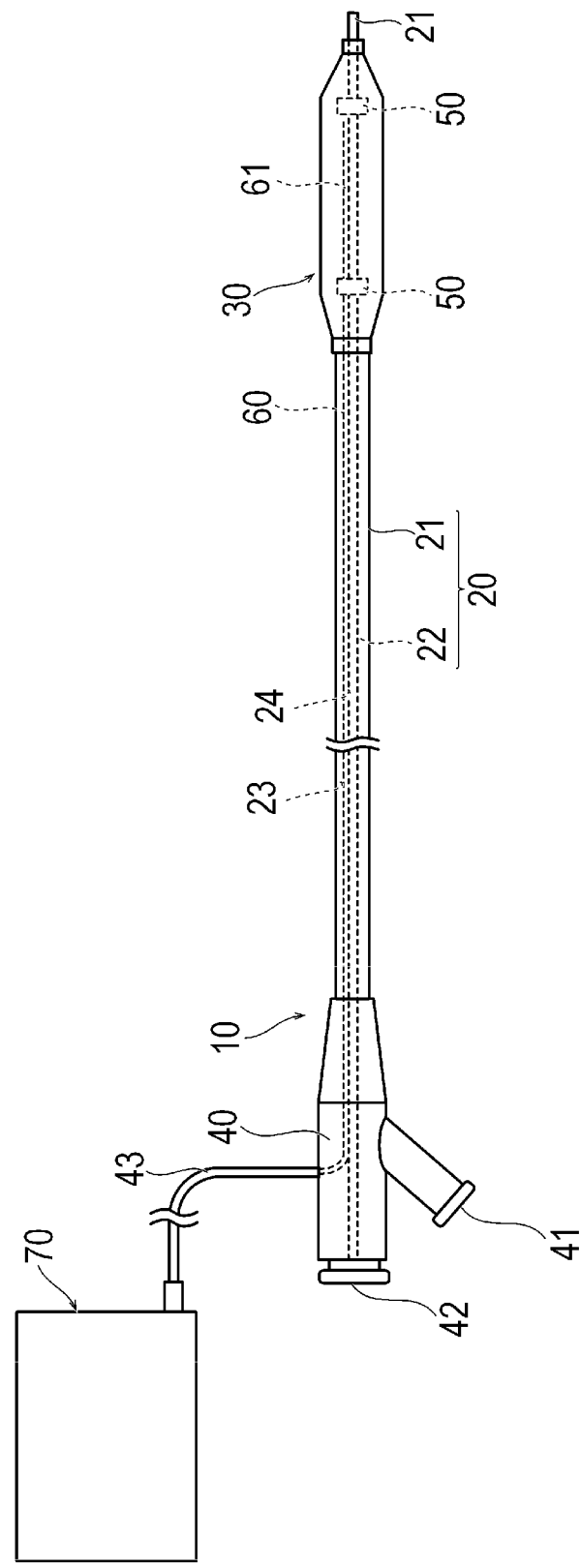
FIG. 1 is a plan view illustrating an irradiation device used in a treatment method according to a first embodiment.

Set forth below with reference to the accompanying drawings is a detailed description of embodiments of an irradiation device used for treatment of cervical cancer and a treatment method for cervical cancer representing examples of the inventive irradiation device used for treatment of cervical cancer and treatment method for cervical cancer. For convenience of explanation, dimensions in the drawings may be exaggerated and may be different from actual dimensions. In the present specification and the drawings, components having substantially the same functional configuration are designated by the same reference numerals, and a duplicate description of the components having substantially the same functional description will be omitted. In the present specification, a side to be inserted into a body lumen of a device is referred to as a "distal side", and a side to be operated is referred to as a "proximal side".

First Embodiment

A treatment method according to a first embodiment is a treatment method for cervical cancer, and is a treatment method related to photoimmunotherapy of killing cancer cells by irradiating an antibody-photosensitive substance bound to cell membranes of the cancer cells with near-infrared light. In this treatment method, the antibody-photosensitive substance, which is obtained by binding an antibody that specifically binds to only a specific antigen on surfaces of the cancer cells and a photosensitive substance paired with the antibody, is used as a drug. The antibody is not particularly limited, and may be, for example, panitumbab, trastuzumab, HuJ591, and the like. The photosensitive substance can be, for example, hydrophilic phthalocyanine which is a substance that reacts with near-infrared light having a wavelength of about 700 nm (IR700), but is not limited to hydrophilic phthalocyanine. IR 700, for example, is capable of killing the cancer cells by absorbing light upon reception of near-infrared light having a wavelength having a peak in the vicinity of 700 nm, and causing a chemical change to form a hole in the cell membrane.

In the treatment method according to the first embodiment, in order to transvascularly and transvaginally irradiate the antibody-photosensitive substance bound to the cancer cells with near-infrared light, an irradiation device 10 that can be inserted into a blood vessel and a cervix is used, as illustrated in FIG. 1. First, the irradiation device 10 will be described.

Figure 2:
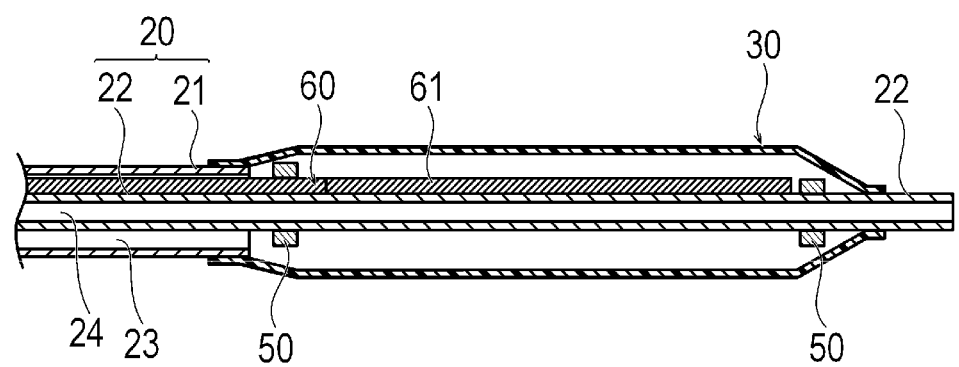
FIG. 2 is a cross-sectional view illustrating a distal portion of the irradiation device.

As illustrated in FIGS. 1 and 2, the irradiation device 10 can include an elongated shaft portion 20, a balloon 30 which is a deformation portion provided at a distal portion of the shaft portion 20, a hub 40 connected to a proximal portion of the shaft portion 20, orientation markers 50, and an optical fiber 60. The irradiation device 10 is used by being connected to a light output device 70.

The shaft portion 20 can include an outer tube 21 which is a tubular body having a distal end and a proximal end, the distal end and the proximal end being open, and an inner tube 22 disposed inside the outer tube 21. An inflation lumen 23 through which an inflation fluid for inflating the balloon 30 flows is formed between the outer tube 21 and the inner tube 22, and a guide wire lumen 24 into which a guide wire 80 can be inserted is formed inside the inner tube 22.

The balloon 30 has a distal side adhered to the inner tube 22, and a proximal side adhered to the outer tube 21. The inside of the balloon 30 communicates with the inflation lumen 23. The balloon 30 can be deformed and inflated upon inflow of the fluid into the balloon 30.

The hub 40 has a first opening portion 41 that communicates with the inflation lumen 23 of the outer tube 21 and that functions as a port for causing the inflation fluid to flow into and out of the first opening portion 41, a second opening portion 42 that communicates with the guide wire lumen 24, and a connection cable 43 for connecting the optical fiber 60 to the light output device 70. The connection cable 43 is detachable from the light output device 70.

The balloon 30 is preferably formed of a material having a certain degree of flexibility, and examples of such a material for the balloon 30 can include polyolefins such as polyethylene, polypropylene, polybutene, an ethylene-propylene copolymer, an ethylene-vinyl acetate copolymer, an ionomer, or a mixture of two or more of polyolefins such as polyethylene, polypropylene, polybutene, an ethylene-propylene copolymer, an ethylene-vinyl acetate copolymer, and an ionomer materials, thermoplastic resins such as a soft polyvinyl chloride resin, a polyamide, a polyamide elastomer, a polyester, a polyester elastomer, polyurethane, and a fluororesin, silicone rubber, and latex rubber.

The light output device 70 can output near-infrared light having any wavelength to the optical fiber 60 at any dose.

The light output device 70 outputs light to the optical fiber 60 such that light can be emitted at a wavelength of, for example, 660 nm to 740 nm and a dose of, for example, 1 $Jcm^{-2}$ to 50 $Jcm^{-2}$.

The optical fiber 60 extends from the hub 40 to the balloon 30 in the inflation lumen 23 along an outer surface of the inner tube 22. The optical fiber 60 may include one fiber or a plurality of bundled fibers. The optical fiber 60 can receive near-infrared light from the light output device 70 via the connection cable 43 provided in the hub 40. The optical fiber 60 has a distal end provided with an irradiation unit 61 for emitting light.

The irradiation unit 61 irradiates the outside with light entering from a proximal side of the optical fiber 60. The irradiation unit 61 may be configured with, for example, a lens, a diffuser, a mirror, or the like. The irradiation unit 61 can be appropriately designed so as to be able to emit near-infrared light by using the lens, diffuser, mirror, or the like in a predetermined direction. A structure of the irradiation unit 61 is not limited as long as the irradiation unit 61 can irradiate the outside with light.

The irradiation unit 61 irradiates, with near-infrared light from the inside of the balloon 30, a range including both a direction substantially perpendicular to an axis of the optical fiber 60 and a substantially distal direction (a direction parallel to the axis of the optical fiber 60). Therefore, near-infrared light can be emitted with a predetermined irradiation angle. Alternatively, the irradiation unit 61 may emit near-infrared light only in the direction substantially perpendicular to the axis of the optical fiber 60 or the substantially distal direction.

The orientation marker 50 is a site for a surgeon to confirm a position in a body. The orientation marker 50 is arranged near the balloon 30 and the irradiation unit 61. A position where the orientation marker 50 is arranged and the number of the orientation marker 50 are not particularly limited, and for example, two orientation markers 50 are arranged on an outer peripheral surface of the inner tube 22 inside the balloon 30. The orientation markers 50 may also be arranged on the outer tube 21, for example. The orientation markers 50 are formed of, for example, an X-ray opaque material. The X-ray opaque material can be, for example, a metal material such as gold, platinum, or tungsten, or an alloy containing these metals. Accordingly, the surgeon can confirm the positions of the orientation markers 50 under an X-ray contrast outside the body. The orientation markers 50 may not be an X-ray contrast marker as long as the surgeon can confirm the position in the body.

Next, the treatment method according to the first embodiment will be described.

Figure 3:
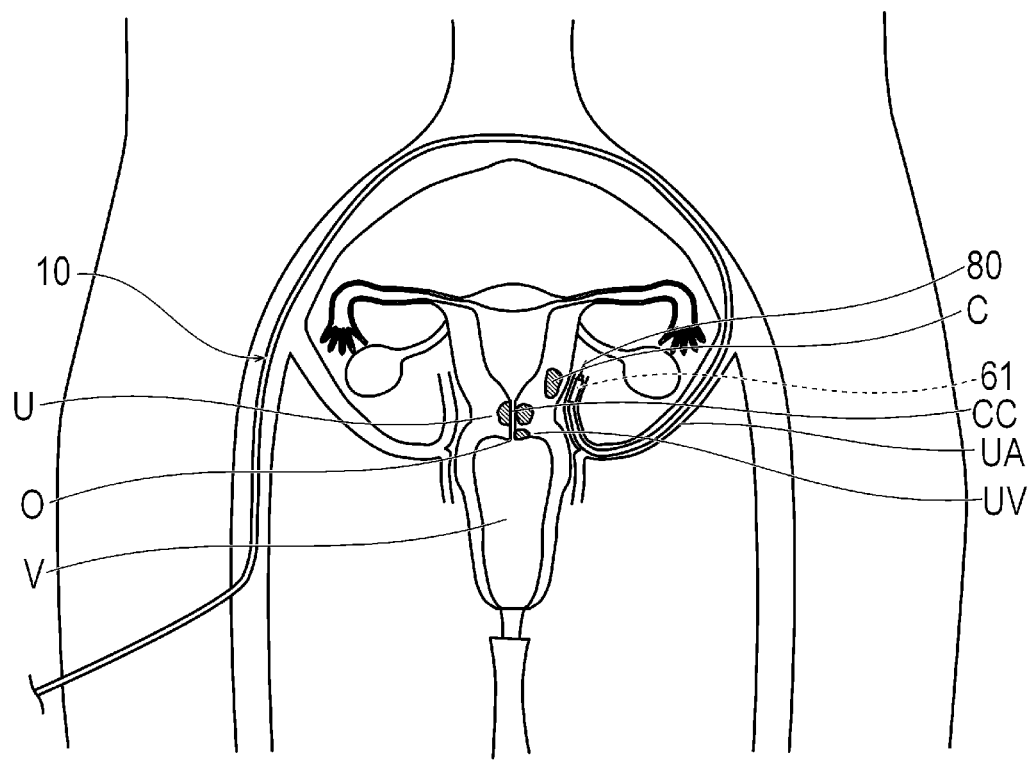
FIG. 3 is a schematic view illustrating a state in a body when the irradiation device is inserted into a uterine artery in the treatment method according to the first embodiment.

First, the antibody-photosensitive substance is administered intravenously. Approximately 12 hours to 36 hours after the intravenous administration, the surgeon inserts the guide wire 80 into the blood vessel, for example, from a femoral artery, as illustrated in FIG. 3. Next, a proximal end of the guide wire 80 is inserted into the guide wire lumen 24 of the irradiation device 10, so as to cause the irradiation device 10 to reach a uterine artery UA through an internal iliac artery along the guide wire 80. Then, the surgeon moves a distal portion of the irradiation device 10 (in particular, the irradiation unit 61) from a cervix U to the vicinity of a tissue or an organ infiltrated with cancer cells C while confirming the positions of the orientation markers 50 under the X-ray contrast. The tissue or the organ in which the cancer cells C are formed is the cervix, a uterine tissue, a pelvis, a bladder wall, a rectal mucosa, or the like. The surgeon arranges the distal portion of the irradiation device 10 at a position where the tissue or the organ infiltrated with the cancer cell C can be irradiated with near-infrared light.

Figure 4:
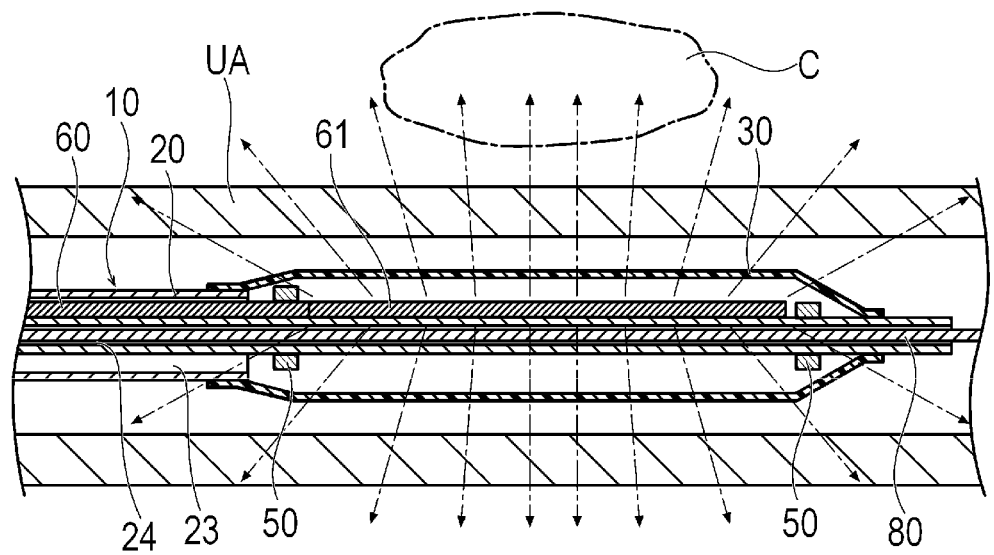
FIG. 4 is a schematic cross-sectional view for illustrating a state where near-infrared light is emitted by using the irradiation device inserted into the uterine artery.

Next, as illustrated in FIG. 4, near-infrared light is emitted from the optical fiber 60. The irradiation with near-infrared light is started 12 hours to 36 hours after the intravenous administration. An irradiation direction of near-infrared light from the optical fiber 60 includes a direction perpendicular to the axis of the optical fiber 60. Therefore, the optical fiber 60 can effectively irradiate the site with near-infrared light from the inside of the blood vessel to the outside of the blood vessel. The optical fiber 60 may emit near-infrared light in the distal direction. The surgeon can appropriately select the optical fiber 60 to be used according to a position of the cancer cells C with respect to the blood vessel into which the irradiation device 10 is inserted.

The surgeon may supply a saline (or saline solution) to the guide wire lumen 24 from a proximal side of the irradiation device 10 before emitting near-infrared light from the optical fiber 60. Accordingly, the saline is injected (flushed) from the irradiation device 10 into the uterine artery UA. As a result, blood in the blood vessel where the distal portion of the irradiation device 10 is positioned is flushed away, which makes the irradiation with near-infrared light less likely to be influenced by the blood. Further, the surgeon may inflate the balloon 30 by supplying the inflation fluid from the inflation lumen 23 into the balloon 30 before emitting near-infrared light from the optical fiber 60. The balloon 30 is in close contact with a blood vessel wall and blocks blood flow. Accordingly, the blood is not present between the balloon 30 and the blood vessel wall, which makes the irradiation with near-infrared light less likely to be influenced by the blood. When the balloon 30 is inflated, the surgeon discharges the inflation fluid from the balloon 30 and contracts the balloon 30 after the irradiation with near-infrared light is completed.

When emitting near-infrared light, near-infrared light reaches the antibody-photosensitive substance bound to cell membranes of the cancer cells C. Accordingly, a chemical change occurs to the photosensitive substance, and a structural change occurs to the antibody-photosensitive substance, whereby a hole is formed in the cell membrane, and the cancer cells C can be killed.

The surgeon stops emitting near-infrared light when the surgeon determines that the cancer cells C have been sufficiently killed, or that further irradiation is not desirable, or when a predetermined time has passed.

Next, the surgeon draws the irradiation device 10 out of the body. Then, the surgeon washes the irradiation device 10. Accordingly, the blood is removed from the irradiation device 10. It is preferable that the blood vessel into which the irradiation device 10 is inserted is not infiltrated with the cancer cells C. Accordingly, the cancer cells C do not attach to the irradiation device 10, and the same irradiation device 10 can be used for a subsequent transvaginal treatment.

Next, the surgeon specifies a position of the cancer cells C irradiated with near-infrared ray, and records the position. It is desirable that the position of the cancer cell C is recorded as electronic data so as to correspond to position information of data such as a CT image and an MRI image of a patient acquired in advance. Accordingly, a subsequent procedure can be relatively smoothly advanced, and post-operative follow-up can be effectively performed. For example, when a plurality of the cancer cells C is irradiated with near-infrared ray, all the cancer cells C can be accurately and reliably irradiated by accurately grasping the tumor for which the irradiation with near-infrared ray is completed. The specification and recording of the position of the cancer cells C is also appropriately performed in a subsequent irradiation with near-infrared ray.

Figures 5A, 5B:
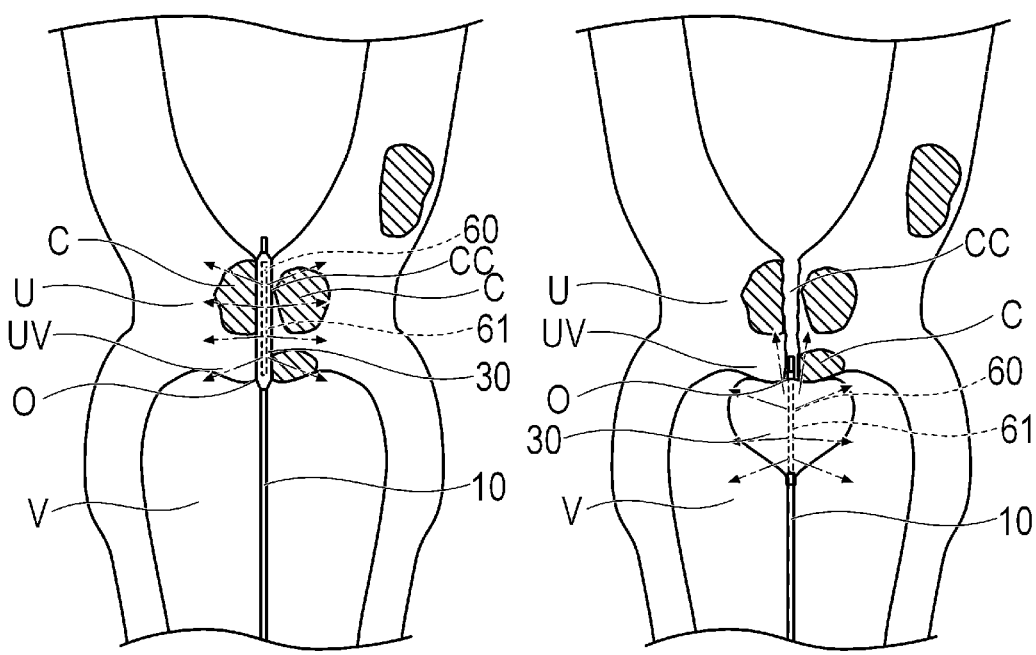

Next, the surgeon inserts the irradiation device 10 which is drawn out from the blood vessel and washed, into a cervical canal CC of the cervix U from a vagina V through an external uterine ostium O, as illustrated in FIG. 5A. Accordingly, the balloon 30 is positioned in the cervical canal CC. Then, the surgeon performs irradiation with near-infrared light from the optical fiber 60. The irradiation direction of near-infrared light from the optical fiber 60 includes the direction substantially perpendicular to the axis of the optical fiber 60. Therefore, the optical fiber 60 can effectively irradiate the cancer cells C positioned in the cervix U with near-infrared light from the cervical canal CC. The optical fiber 60 may emit near-infrared light in the distal direction. The surgeon may insert the irradiation device 10 different from the irradiation device 10 drawn out from the blood vessel and washed into the cervical canal CC from the vagina V. When emitting near-infrared light from the cervical canal CC, since the cervical canal CC is narrow, the distal portion of the irradiation device 10 is in close contact with the cervix U. Therefore, the balloon 30 does not need to be inflated. The balloon 30 may be inflated in a lumen of the cervix U.

When emitting near-infrared light, near-infrared light reaches the antibody-photosensitive substance bound to the cell membranes of the cancer cells C in the cervix U. Accordingly, the chemical change of the photosensitive substance occurs, and the structural change of the antibody-photosensitive substance occurs, whereby the hole is formed in the cell membrane, and the cancer cells C in the cervix U irradiated with near-infrared light is killed.

The surgeon stops emitting near-infrared light when the surgeon determines that the cancer cells C have been sufficiently killed, or that further irradiation is not desirable, or when the predetermined time has passed.

Next, the surgeon draws out the irradiation device 10, and draws out at least a part (or all) of the balloon 30 and the irradiation unit 61 from the external uterine ostium O. Thereafter, the surgeon supplies the inflation fluid into the balloon 30 from the inflation lumen 23 to inflate the balloon 30 as illustrated in FIG. 5B. Then, the surgeon pushes the irradiation device 10, and presses a distal portion of the inflated balloon 30 against a uterine vagina UV. The uterine vagina UV is a site on a vagina V side of the cervix U, and on which the external uterine ostium O is formed. Therefore, the balloon 30 is in close contact with the vicinity of the external uterine ostium O of the uterine vagina UV, and is inflated so as to follow a shape of the uterine vagina UV (organ). When a part of the balloon 30 is positioned in the cervical canal CC, even if the surgeon does not push the irradiation device 10, the balloon 30 may be held in close contact with the vicinity of the external uterine ostium O of the uterine vagina UV.

Then, the surgeon performs irradiation with near-infrared light from the optical fiber 60. The irradiation direction of near-infrared light from the optical fiber 60 includes the substantially distal direction and/or the direction substantially perpendicular to the axis of the optical fiber 60. Near-infrared light emitted in the distal direction from the optical fiber 60 can effectively reach the cancer cells C positioned in the uterine vagina UV. Near-infrared light emitted in the direction perpendicular to the axis of the optical fiber 60 from the optical fiber 60 also reaches the cancer cells C positioned at a site away from the external uterine ostium O of the uterine vagina UV in a direction different from that of the irradiation illustrated in FIG. 5A, and can effectively reach the cancer cells C positioned in the vagina V. Therefore, the optical fiber 60 can effectively emit near-infrared light to the cancer cells C positioned in the uterine vagina UV and the vagina V.

The surgeon stops emitting near-infrared light when the surgeon determines that the cancer cells C have been sufficiently killed, or that further irradiation is not desirable, or when a predetermined time has passed. Next, the surgeon discharges the inflation fluid from the balloon 30 to contract the balloon 30.

Next, the surgeon rotates the irradiation device 10 by a predetermined angle about an axial center of the irradiation device 10. The angle to be rotated is not particularly limited, and can be, for example, 90° to 180°. Then, the surgeon inflates the balloon 30 again in the same manner as described above, and brings the balloon 30 into close contact with the vicinity of the external uterine ostium O of the uterine vagina UV. The balloon 30 is inflated so as to follow the shape of the uterine vagina UV (organ). Thereafter, the surgeon performs irradiation with near-infrared light from the optical fiber 60. Accordingly, the cancer cells C at different positions of the uterine vagina UV and the vagina V can be irradiated with near-infrared light by emitting near-infrared light at a place different from that before the rotation. Thereafter, the surgeon stops emitting near-infrared light. A series of processes in which the rotation of the irradiation device 10, the inflation of the balloon 30, the irradiation with near-infrared light, the stop of the irradiation, and the contraction of the balloon 30 are combined can be repeated once or more. This series of processes may not be performed even once. Thereafter, the surgeon draws the irradiation device 10 out of the body. Accordingly, this treatment method is ended.

As described above, the treatment method according to the first embodiment is a treatment method for cervical cancer, including: intravenously administering the antibody-light-absorbing substance; inserting the first irradiation device 10, including the first optical fiber 60 and the orientation markers 50, into the uterine artery UA 12 hours to 36 hours after the intravenous administration; advancing the irradiation device 10 to the target position while confirming the position of the first irradiation device 10 with the orientation markers 50; emitting near-infrared light by using the first optical fiber 60 in the direction substantially perpendicular to the first optical fiber 60; removing the first irradiation device 10 out of the body; inserting the second irradiation device 10, which is the first irradiation device 10 or another irradiation device 10, from the vagina V into the cervix U; performing irradiation by using the second optical fiber 60 included in the second irradiation device 10 in the direction substantially perpendicular to the second optical fiber 60; drawing at least a part of the deformation portion included in the second irradiation device 10 to the external uterine ostium O and inflating the balloon 30, which is the deformation portion, so as to follow the shape of the organ; emitting near-infrared light by using the second optical fiber 60 in the substantially distal direction and/or the direction substantially perpendicular to the second optical fiber 60; and contracting the balloon 30.

In the treatment method configured as described above, the first irradiation device 10 is inserted into the uterine artery UA to emit near-infrared light from the inside of the blood vessel in the substantially vertical direction, so that the tissue or the organ infiltrated with the cancer cells C near the uterine artery UA can be effectively irradiated with near-infrared light. Further, in this treatment method, the second irradiation device 10 is inserted into the narrow cervical canal CC to emit near-infrared light in the substantially vertical direction, so that the cancer cells C in the cervix U can be effectively irradiated with near-infrared light from the cervical canal CC of the cervix U. Furthermore, in this treatment method, the balloon 30, which is the deformation portion drawn from the external uterine ostium O, is inflated to emit near-infrared light in the distal direction and/or the vertical direction, so that cervical cancer near the uterine vagina UV can be effectively irradiated with near-infrared light. Therefore, in this treatment method, the antibody-photosensitive substance bound to the cell membranes of the cancer cells C in the cervix U and the cancer cells C in the tissue or the organ infiltrated from the cervix U can be effectively irradiated with near-infrared light. This treatment method is effective not only in an early stage where the cancer cells C are confined to the cervix but also in stage IIB where the cancer cells C infiltrate into a parametrium, stage IIIA where vaginal wall infiltration reaches the lower third of the vagina, stage IIIB where the infiltration into the parametrium reaches the pelvic wall, and stage IVA where the cancer cells C infiltrate into the bladder and rectal mucosa.

In this treatment method, the rotating the second irradiation device 10, the inflating the balloon 30 so as to follow the shape of the organ, the emitting near-infrared light by using the second optical fiber 60 in the substantially distal direction and/or the direction substantially perpendicular to the second optical fiber 60, and the contracting the balloon 30 are repeated at least once after the contracting the balloon 30, which is the deformation portion. Accordingly, in this treatment method, a wide area of the cervix U in a circumferential direction can be irradiated with near-infrared light. Further, in this treatment method, the vagina V can also be irradiated with near-infrared light in a wide area in the circumferential direction.

The second irradiation device 10 can be identical to the first irradiation device 10. Accordingly, in this treatment method, the irradiation with near-infrared light from the uterine artery UA and the irradiation with near-infrared light from the cervix U can be performed by one irradiation device 10. Therefore, this treatment method can help improve medical economics. The second irradiation device 10 may not be identical to the first irradiation device 10.

In this treatment method, after the removing the first irradiation device 10 out of the body, the first irradiation device 10 is washed. Accordingly, in this treatment method, the blood attached to the first irradiation device 10 inserted into the blood vessel is removed, and the first irradiation device 10 can be placed in a desirable state to be inserted from the vagina V into the cervix U.

In this treatment method, the inflating the balloon 30 included in the first irradiation device 10 may be performed before the emitting near-infrared light by using the first optical fiber 60, and the contracting the balloon 30 included in the first irradiation device 10 may be performed after the emitting near-infrared light by using the first optical fiber 60. Accordingly, when emitting near-infrared light from the first irradiation device 10 in the uterine artery UA, the blood flow in the uterine artery UA can be blocked. Therefore, an influence of the blood on near-infrared light can be reduced, and a target site can be effectively irradiated with near-infrared light.

In the first embodiment, the treatment device may not be inserted into the blood vessel. That is, a modification of the treatment method according to the first embodiment is a treatment method for cervical cancer, including: intravenously administering an antibody-light-absorbing substance; inserting the second irradiation device 10 including the second optical fiber 60 from the vagina V into the cervix U 12 to 36 hours after the intravenous administration; performing irradiation by using the second optical fiber 60 included in the second irradiation device 10 in the direction substantially perpendicular to the second optical fiber 60; drawing at least a part of the balloon 30 included in the second irradiation device 10 to the external uterine ostium O and inflating the balloon 30 so as to follow the shape of the organ; emitting near-infrared light by using the second optical fiber 60 in the substantially distal direction and/or the direction substantially perpendicular to the second optical fiber 60; and contracting the balloon 30.

In the treatment method configured as described above, the irradiation device 10 is inserted into the thin cervix U and the balloon 30 is inflated to emit near-infrared light in the distal direction and/or the vertical direction, so that cervical cancer in a wide range of the cervix U can be effectively irradiated with near-infrared light. Therefore, in this treatment method, the antibody-photosensitive substance bound to the cell membranes of the cancer cells C in the cervix U can be effectively irradiated with near-infrared light. This treatment method is effective not only in the early stage where the cancer cells C are confined to the cervix but also in stage IIA and stage IIIA where the cancer cells C infiltrate into a vaginal wall.

Second Embodiment

A treatment method according to a second embodiment is a method of inserting the irradiation device 10 from the vagina V into the cervix U, but is different from the treatment method according to the first embodiment. The irradiation device 10 to be used is the same as the irradiation device 10 used in the treatment method according to the first embodiment.

In the treatment method according to the second embodiment, a surgeon inserts the irradiation device 10 into the uterine artery UA, and irradiates a tissue or an organ infiltrated with the cancer cells C with near-infrared light from the uterine artery UA, in the same manner as in the first embodiment.

Figure 6:
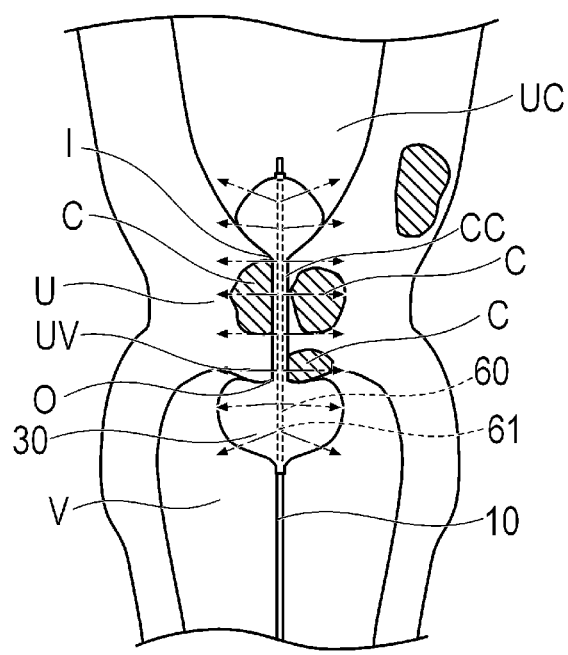
FIG. 6 is a schematic view illustrating a state where near-infrared light is emitted by using an irradiation device inserted into a cervix from a vagina in a treatment method according to a second embodiment.

The surgeon draws the irradiation device 10 out of the body from a blood vessel, washes the irradiation device 10, and then inserts the irradiation device 10 from the vagina V through the external uterine ostium O into the cervical canal CC as illustrated in FIG. 6. Accordingly, the distal portion of the balloon 30 is arranged in a uterine cavity UC on a side distal of an internal cervical ostium I, and a proximal portion of the balloon 30 is arranged in the vagina V on a side proximal of the external uterine ostium O. Therefore, the balloon 30 penetrates the cervical canal CC. Then, the surgeon performs irradiation with near-infrared light from the optical fiber 60. Accordingly, the optical fiber 60 arranged in the cervical canal CC can effectively irradiate the cancer cells C positioned in the cervix U with near-infrared light. A distal portion of the optical fiber 60 arranged in the uterine cavity UC can effectively irradiate the cancer cells C positioned in the uterine cavity UC and the cervix U close to the uterine cavity UC with near-infrared light. A proximal portion of the optical fiber 60 arranged in the vagina V can effectively irradiate the cancer cells C positioned in the uterine vagina UV and the vagina V with near-infrared light.

As described above, the treatment method according to the second embodiment is a treatment method for cervical cancer, including: intravenously administering an antibodylight-absorbing substance; inserting the first irradiation device 10, including the first optical fiber 60 and the orientation markers 50, into the uterine artery UA 12 hours to 36 hours after the intravenous administration; advancing the irradiation device 10 to the target position while confirming the position of the first irradiation device 10 with the orientation markers 50; emitting near-infrared light by using the first optical fiber 60 in the direction substantially perpendicular to the first optical fiber 60; removing the first irradiation device 10 out of the body; inserting the second irradiation device 10, which is the first irradiation device 10 or another irradiation device 10, from the vagina V into the cervix U; inflating the balloon 30 included in the second irradiation device 10 so as to follow the shape of the organ; the emitting near-infrared light by using the second optical fiber 60 in the substantially distal direction and/or the direction substantially perpendicular to the second optical fiber 60; and contracting the balloon 30.

In the treatment method configured as described above, the first irradiation device 10 is inserted into the uterine artery UA to emit near-infrared light from the inside of the blood vessel in the substantially vertical direction, so that the tissue or the organ infiltrated with the cancer cells C near the uterine artery UA can be effectively irradiated with near-infrared light. Further, in this treatment method, the second irradiation device 10 is inserted into the thin cervix U and the balloon 30 is inflated to emit near-infrared light in the distal direction and/or the vertical direction, so that cervical cancer in a wide range of the cervix U can be effectively irradiated with near-infrared light. Therefore, in this treatment method, the antibody-photosensitive substance bound to cell membranes of the cancer cells C at both sites such as the cervix U and the infiltrated pelvic wall can be effectively irradiated with near-infrared light. This treatment method is effective not only in an early stage where the cancer cells C are confined to the cervix but also in stage IIB where the cancer cells C infiltrate into the parametrium, stage IIIA where vaginal wall infiltration reaches the lower third of the vagina, stage IIIB where the infiltration into the parametrium reaches the pelvic wall, and stage IVA where the cancer cells C infiltrate into the bladder and the rectal mucosa.

In the second embodiment, the treatment device may not be inserted into the blood vessel. That is, a modification of the treatment method according to the second embodiment is a treatment method for cervical cancer, including: intravenously administering an antibody-light-absorbing substance; inserting the irradiation device 10 including the second optical fiber 60 from the vagina V into the cervix U 12 hours to 36 hours after the intravenous administration; inflating the balloon 30 included in the irradiation device 10 so as to follow the shape of the organ; emitting near-infrared light by using the optical fiber 60 in the substantially distal direction and/or the direction substantially perpendicular to the optical fiber 60; and contracting the balloon 30.

In the treatment method configured as described above, the irradiation device 10 is inserted into the thin cervix U and the balloon 30 is inflated to emit near-infrared light in the distal direction and/or the vertical direction, so that cervical cancer in a wide range of the cervix U can be effectively irradiated with near-infrared light. Therefore, in this treatment method, the antibody-photosensitive substance bound to the cell membranes of the cancer cells C in the cervix U can be effectively irradiated with near-infrared light. This treatment method is effective not only in the early stage where the cancer cells C are confined to the cervix but also in stage IIA and stage IIIA where the cancer cells C infiltrate into the vaginal wall.

Further, in this treatment method, in the inflating the balloon 30, which is a deformation portion, a part of the balloon 30 may be inflated so as to follow a shape of the uterine vagina UA on the side proximal of the external uterine ostium O. The distal portion of the balloon 30 may be positioned in the cervix U or in the uterine cavity UC. Accordingly, in this treatment method, the antibody-photosensitive substance bound to the cell membranes of the cancer cells in the cervix U including the uterine vagina UV and the tissue or the organ infiltrated downward of the cervix U can be effectively irradiated with near-infrared light.

Further, in this treatment method, in the inflating the balloon 30, which is the deformation portion, the proximal portion of the balloon 30 may be inflated so as to follow the shape of the uterine vagina UV at the side proximal of the external uterine ostium O, and the distal portion of the balloon 30 may be inflated so as to follow a shape of the uterine cavity UC at the side distal of the internal cervical ostium I. Accordingly, in this treatment method, the antibody-photosensitive substance bound to the cell membranes of the cancer cells of the cervix U and the tissue or the organ infiltrated from the cervix U in the vertical direction can be effectively irradiated with near-infrared light.

Figure 7A:
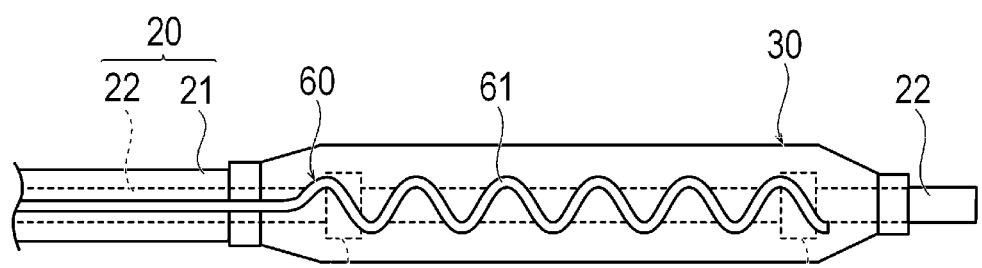
Figure 7B:
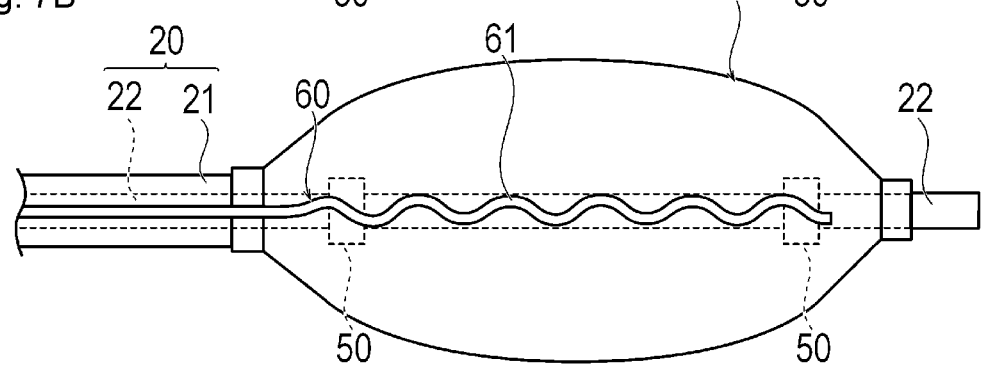

The disclosure is not limited to the embodiments described above, and various modifications can be made by those skilled in the art within a scope of the technical idea of the disclosure. For example, as in a first modification of the irradiation device 10 illustrated in FIG. 7A, the irradiation unit 61 of the optical fiber 60 may be arranged not in the balloon 30 but on an outer surface side of the balloon 30. The number of the optical fiber 60 may be either one or two or more. Accordingly, a distance from the irradiation unit 61 to the cancer cells C can be shortened, so that loss of light energy can be reduced and near-infrared light can be caused to effectively reach the cancer cells C. Unlike the balloon 30, the optical fiber 60 has no elasticity. Therefore, for example, as illustrated in FIG. 7B, the optical fiber 60 is preferably meandered or coiled such that the optical fiber 60 can be deformed following the inflation and the contraction of the balloon 30.

Figure 8A:
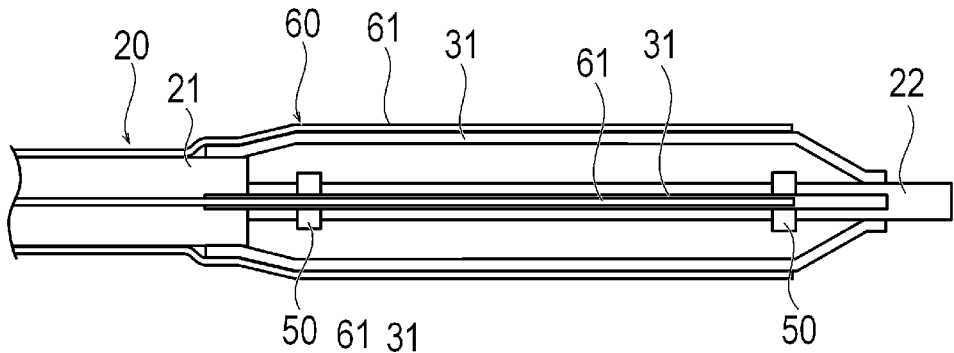
Figure 8B:
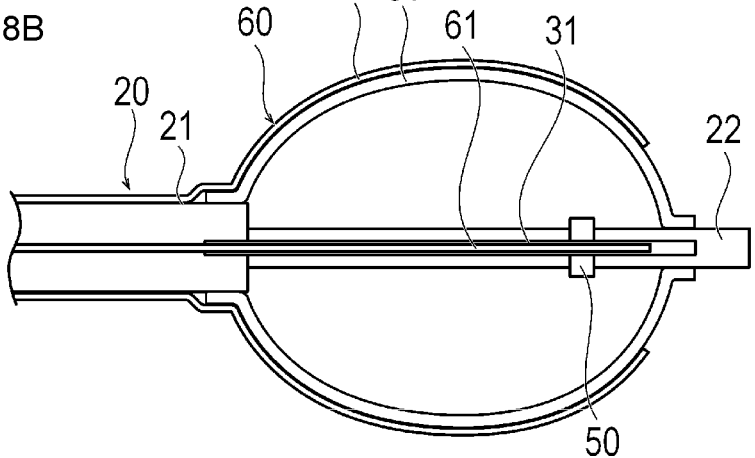

For example, as in a second modification of the irradiation device 10 illustrated in FIG. 8A, the deformation portion may be at least one wire member 31 instead of the balloon 30. The wire member 31 has a distal portion fixed to the inner tube 22, and a proximal portion fixed to the outer tube 21. In the second modification, the inner tube 22 and the outer tube 21 are relatively movable in the axial direction. Therefore, by bringing a distal end of the inner tube 22 and the distal end of the outer tube 21 closer to each other in the axial direction, each wire member 31 receives a compressive force, and is deformable so as to be convex outward in a radial direction, as illustrated in FIG. 8B. Each wire member 31 has an outer surface arranged with the irradiation unit 61 of the optical fiber 60. Therefore, a distance from the irradiation unit 61 to the cancer cells C can be shortened, so that the loss of the light energy can be reduced and near-infrared light can be caused to effectively reach the cancer cells C.

Figure 9A:
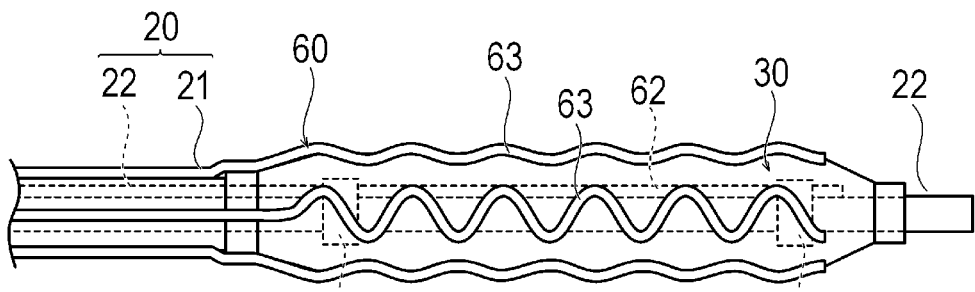
Figure 9B:
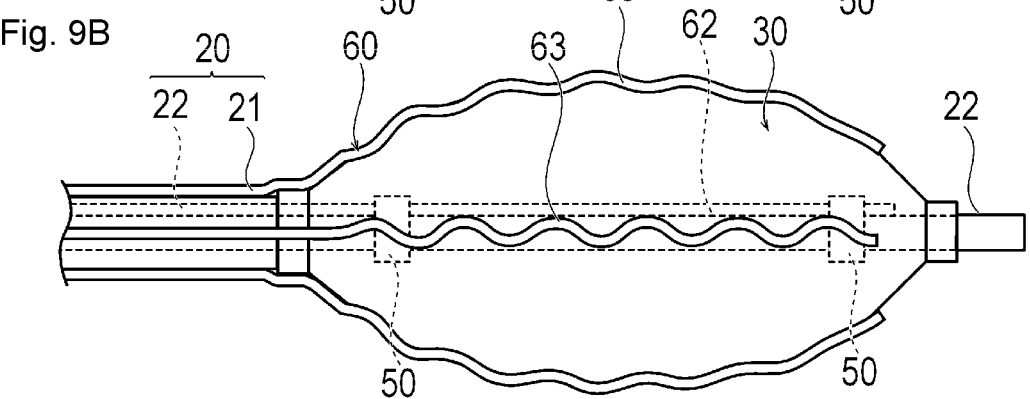

For example, as in a third modification of the irradiation device 10 illustrated in FIG. 9A, the deformation portion is the balloon 30, and the optical fiber 60 may include an inner optical fiber 62 arranged inside the balloon 30 and outer optical fibers 63 arranged on the outer surface of the balloon 30. The inner optical fiber 62 emits near-infrared light in a substantially distal direction, for example. The outer optical fiber 63 emits near-infrared light in a range including a direction perpendicular to an axis of the outer optical fiber 63 and the distal direction. Accordingly, a distance from the irradiation unit 61 of the outer optical fiber 63 to the cancer cells C can be shortened, so that the loss of the light energy can be reduced and near-infrared light can be caused to effectively reach the cancer cells C. Further, the inner optical fiber 62 can effectively perform irradiation in the distal direction. Unlike the balloon 30, the outer optical fiber 63 has no elasticity. Therefore, for example, as illustrated in FIG. 9B, the outer optical fiber 63 is preferably meandered or coiled such that the outer optical fiber 63 can be deformed following the inflation and the contraction of the balloon 30.

The detailed description above describes embodiments of an irradiation device used for treatment of cervical cancer and a treatment method for cervical cancer. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method for cervical cancer, comprising:
   intravenously administering an antibody-light-absorbing substance;
   inserting a first irradiation device including a first optical fiber from a vagina into a cervix 12 hours to 36 hours after the intravenous administration;
   performing irradiation by using the first optical fiber included in the first irradiation device in a direction substantially perpendicular to the first optical fiber;
   drawing at least a part of a deformation portion included in the first irradiation device to an external uterine ostium and inflating the deformation portion so as to follow a shape of an organ;
   emitting near-infrared light by using the first optical fiber in a substantially distal direction and/or the direction substantially perpendicular to the first optical fiber; and
   contracting the deformation portion.

2. The treatment method according to claim 1, wherein in the inflating the deformation portion, inflating a part of the deformation portion to follow a shape of a uterine vagina on a side proximal of an external uterine ostium.

3. The treatment method according to claim 1, wherein in the inflating the deformation portion, inflating a proximal portion of the deformation portion to follow a shape of a uterine vagina on a side proximal of an external uterine ostium, and inflating a distal portion of the deformation portion to follow a shape of a uterine cavity on a side distal of an internal cervical ostium.

4. The treatment method according to claim 1, further comprising:
   rotating the first irradiation device;
   following the shape of the organ in the inflating the deformation portion;
   using the first optical fiber in the substantially distal direction and/or the direction substantially perpendicular to the first optical fiber in the emitting near-infrared light; and
   repeating the contracting the deformation portion at least once after the contracting the deformation portion.

5. A treatment method for cervical cancer, the method comprising:
   intravenously administering an antibody-light-absorbing substance;
   inserting a first irradiation device including a first optical fiber from a vagina into a cervix 12 hours to 36 hours after the intravenous administration;
   inflating a deformation portion included in the first irradiation device so as to follow a shape of an organ;
   emitting near-infrared light by using the first optical fiber in a substantially distal direction and/or a direction substantially perpendicular to the first optical fiber; and
   contracting the deformation portion.

6. The treatment method according to claim 5, wherein in the inflating the deformation portion, inflating a part of the deformation portion to follow a shape of a uterine vagina on a side proximal of an external uterine ostium.

7. The treatment method according to claim 5, wherein in the inflating the deformation portion, inflating a proximal portion of the deformation portion to follow a shape of a uterine vagina on a side proximal of an external uterine ostium, and inflating a distal portion of the deformation portion to follow a shape of a uterine cavity on a side distal of an internal cervical ostium.

8. The treatment method according to claim 5, further comprising:
   rotating the first irradiation device;
   following the shape of the organ in the inflating the deformation portion;
   using the first optical fiber in the substantially distal direction and/or the direction substantially perpendicular to the first optical fiber in the emitting near-infrared light; and
   repeating the contracting the deformation portion at least once after the contracting the deformation portion.

* * * * *